United States Patent [19]

Barker et al.

[11] Patent Number: 4,562,214
[45] Date of Patent: Dec. 31, 1985

[54] PERSONAL CARE EMULSION

[75] Inventors: Graham Barker, Fair Lawn; Martin J. Barabash, Montvale, both of N.J.

[73] Assignee: Witco Chemical Corporation, New York, N.Y.

[21] Appl. No.: 229,238

[22] Filed: Jan. 28, 1981

Related U.S. Application Data

[63] Continuation-in-part of Ser. No. 74,023, Sep. 10, 1979, abandoned.

[51] Int. Cl.$^4$ .................. A61K 47/00; B01J 13/00
[52] U.S. Cl. .................... 514/844; 252/309; 252/312; 514/847
[58] Field of Search ............... 424/358, 168; 514/937

[56] References Cited

U.S. PATENT DOCUMENTS

| | | | |
|---|---|---|---|
| 3,914,131 | 10/1975 | Hutchison | 106/268 |
| 3,919,430 | 11/1975 | Siegel | 424/365 |
| 4,035,514 | 7/1977 | Davis | 424/365 |

FOREIGN PATENT DOCUMENTS

| | | | |
|---|---|---|---|
| 1553145 | 12/1968 | France | 424/358 |
| 12348 | of 1900 | United Kingdom | 424/358 |
| 429185 | 5/1935 | United Kingdom | 424/358 |
| 1004174 | 9/1965 | United Kingdom | 424/358 |

*Primary Examiner*—Dale R. Ore
*Attorney, Agent, or Firm*—Wallenstein, Wagner, Hattis, Strampel & Aubel, Ltd.

[57] ABSTRACT

Emulsifiable compositions of cosmetic emulsion oils, oxidized petrolatum and water, and stable emulsified water-in-oil personal care preparations produced therefrom by neutralizing the acidic functionality of the oxidized petrolatum with a polyvalent cationic water-soluble metal salt.

7 Claims, No Drawings

PERSONAL CARE EMULSION

The present application is a continuation-in-part of U.S. application Ser. No. 074,023, filed 10 Sept. 1979, now abandoned.

BACKGROUND OF THE INVENTION

Heretofore it was known to blend petrolatums and petroleum waxes with various materials to impart a carboxylic character to the petrolatums and waxes. In Hutchinson, U.S. Pat. No. 3,914,131 granted Oct. 21, 1975, there is disclosed blending high molecular weight branched monocarboxylic acids with microcrystalline petroleum wax and mixed glycerols of saturated mono- and dicarboxylic acids. The resultant blended wax was said to be useful in cosmetic formulations. Davis, U.S. Pat. No. 4,035,514 granted July 12, 1977, discloses blends of petrolatum with cetyl alcohol, lanolin alcohols, and alkoxylated fatty acid esters of sorbitol for water dispersion cream uses. Seigel, U.S. Pat. No. 3,919,430 granted Nov. 11, 1974, also discloses blending petrolatums with alcohols and esters for water-in-oil emulsions.

While in the prior art the use of petrolatum and microcrystalline wax is abundantly disclosed and in U.S. Pat. No. 3,914,131, cited above, the use of oxidized microcrystalline waxes is suggested, there is no indication that oxidized petrolatum, as hereinafter disclosed, is usable to form stable water-in-oil emulsions for personal care preparations.

Oxidation of petrolatum to provide, in situ, a degree of carboxylic functionality was generally limited to modest levels of oxidation. More specifically, oxidized petrolatums with relatively low acid numbers of up to about 50 were regarded as useful in rust prevention formulations, but were not considered for personal care preparations. In the first place, their acid numbers were low and they exhibited undesirable aesthetic characteristics, particularly as to color (dark) and odor. Upon increasing the acid number by oxidation, the petrolatums would rapidly take on characteristics which rendered them unsuitable for use in personal care preparations.

In parent U.S. application Ser. No. 074,023, filed 10 Sept. 1979, the following patents were recorded during prosecution:

| No. | Patent No. | Date | Patentee or Agent | Country |
|---|---|---|---|---|
| (1) | 12,348 | 6/1900 | Boleg | Great Britain |
| (2) | 429,185 | 5/1935 | Lean | " |
| (3) | 1,004,174 | 9/1965 | Shiseido | " |
| (4) | 1,553,145 | 12/1968 | L'Oreal | France |

Reference (1), supra, teaches, simply, oxidation of mineral oils in the presence of caustic soda lye to make them water-soluble and useful in medicaments. Reference (2) prepares pesticides by oxidizing waxes or liquid petroleum distillates at elevated temperatures and pressures in the presence of a "known oxidation catalyst", and by subsequently saponifying saponifiables in the resultant reaction mixture. References (3) and (4) are not concerned with oxidized petrolatum, let alone the emulsifiable compositions and stable emulsified W/O personal care preparations herein described.

As will be seen hereinafter, the present invention provides an emulsifiable personal care preparation wherein the petrolatum is readily emulsifiable and provides a stable emulsion which is aesthetically acceptable in odor and color.

THE INVENTION

The present invention relates to emulsifiable compositions useful for preparing stable water-in-oil (W/O) emulsified personal care preparations. More particularly, the instant discovery concerns emulsifiable compositions comprising a cosmetic emulsion oil, such as mineral oil, a refined oxidized petrolatum, and water. Stable, emulsified W/O personal care preparations are prepared therefrom by neutralizing the acidic functionality of the oxidized petrolatum with a polyvalent cationic water-soluble metal salt capable of enhancing the formation of W/O emulsions. Typical such metal salts are sodium borate and saccharated lime. As will be seen hereinafter, additives may be present in these preparations, including (i) other cosmetic oils, such as fatty alcohol esters, natural and/or synthetic waxes, (ii) co-emulsifiers, (iii) preservatives, (iv) and the like.

Not just any oxidized petrolatum is suitable for the emulsifiable compositions and cosmetic preparations of the present invention. In fact, it is important that the petrolatum which is oxidized be of a refined grade and that the resulting oxidized petrolatum exhibit the following characteristics:

| | Range | |
|---|---|---|
| | Broad | Preferred |
| Acid No. (ASTM D-974) | 15–100 | 35–75 |
| Saponification No. | 75–150 | 80–125 |
| Lovibond Color, 2" Cell | 40y, 5r–9r | 40y, 5r–6r |

Suitable refined grade petrolatums for oxidation according to the present invention are of the quality described in the latest National Formulary (N.F.) and the latest U.S. Pharmacopoeia (U.S.P.). Typical is so-called Snow Petrolatum (S.S.216a).

The oxidized petrolatum is best prepared by passing an oxygen-containing gas (e.g., air) through a petrolatum under conditions required to produce oxidized petrolatum of the aforementioned characteristics. Where air is employed, flow rates can be up to 7 cubic feet/minute, and preferably 2 to 4 cubic feet/minute, at temperatures from about 200° F. to 250° F. The air flow of between 2 to 4 cubic feet/minute is not critical. It is preferred because this is a practical (safe) rate of air feed, functionally. Periods of 100 to 200 hours have generally been found useful to produce the desired oxidized petrolatum suitable for the personal care preparation of the present invention. Heating for periods under about 100 hours, while passing an oxygen-containing gas through the petrolatum at temperatures of less than about 200° F., yields an oxidized petrolatum which for the most part is unsatisfactory for personal care preparations. That is to say, because of color, odor, acid number, saponification number, and the like, or combinations of these properties, the oxidized product would detract from the aesthetic value of the personal care product.

Typically, the emulsifiable compositions of the instant invention have the following concentrations:

| Component | Concentration (wt. %) |
|---|---|
| Cosmetic emulsion oil (e.g., | 5–50 |

-continued

| Component | Concentration (wt. %) |
|---|---|
| mineral oil) | |
| Oxidized petrolatum | 1–10 |
| Water | quantum sufficit (q.s.) |

To achieve the stable W/O emulsified cosmetic preparations of the present invention, these emulsifiable compositions are blended with a water phase containing neutralizing agent of the type hereinbefore described and, as desired, with additional cosmetic oils and/or waxes. For best results, the following concentrations of oxidized petrolatum, cosmetic emulsion oil (e.g., mineral oil), neutralizing agent and water in the W/O personal care preparation herein contemplated are as follows:

| Components | Concentration Ranges | |
|---|---|---|
| | Broad | Preferred |
| Cosmetic emulsion oil | 2.5–75.0 | 3.0–60.0 |
| Oxidized petrolatum | 0.5–7.5 | 0.7–6.5 |
| Metal salt | 0.2–2.0 | 0.4–1.0 |

Repeating, other components in conventional quantities may be present in the W/O emulsion preparations.

"Cosmetic emulsion oils" contemplated herein and suitable for the W/O emulsified preparations of the present invention are mineral and/or other hydrocarbon oils, such as squalene, squalane, and the like. If desired, natural and/or synthetic waxes may be added, such as beeswax, spermaceti, paraffin, petrolatum, microcrystalline wax, hydroxyethyl stearamide, cetyl stearate, stearic diethanolamide, and the like. Also, as suggested hereinbefore, conventional quantities of fatty alcohol esters may be present, such as stearyl alcohol esters of $C_{12}$–$C_{18}$ fatty acids, isostearyl alcohol esters of $C_{12}$–$C_{18}$ fatty acids, oleyl alcohol esters of $C_{12}$–$C_{18}$ fatty acids, and the like.

One or more co-emulsifiers may likewise be present. Illustrative co-emulsifiers are: phosphated glycerides, aluminum and calcium stearates, and the like. The phosphated glycerides are the alkali metal phosphoric acid ester salts of partial glycerides, i.e., the ester salts of mono- and di-glycerides which may be prepared in a number of ways. Generally, a derivative of phosphorus, such as phosphorus pentoxide, a polyphosphoric acid, or anhydrous phosphoric acid is reacted with the mono- or di-glyceride, or mixtures thereof, the fatty acid ester moiety or moieties of the glyceride being saturated and/or unsaturated(mono- or di-).

These and other methods of preparing the phosphated mono- and di-glycerides are taught in the art. Illustrative literature is the following: U.S. Pat. Nos. 2,026,785, 2,177,983, 2,177,984, 3,248,229 and 3,875,196; British Pat. No. 1,174,789; Japanese Patent Publication No. 14322/68; German Pat. No. 719,830; Chem. Ber. 71, 1071(1938); and Chem.Ber. 71, 1505(1938).

In U.S. Pat. No. 3,875,196, for instance, phosphoric acid esters of mono- or di-glycerides are prepared by reacting a mono- or di-glyceride ester of stearic acid, myristic acid, palmitic acid, palmitoleic acid, or a mixed acid ester thereof, with a polyphosphoric acid. The polyphosphoric acid is prepared by heating phosphoric acid or by heat treating phosphoric acid with phosphorus pentoxide.

According to U.S. Pat. No. 3,875,196, the corresponding ester salts of the phosphated mono- and di-glycerides are prepared by neutralizing the glyceride ester. For exammple, glyceride ester crystals recovered from the reactions of a polyphosphoric acid and, say, a mono-glyceride, are neutralized with an aqueous sodium hydroxide solution and the monosodium phosphoric acid ester of the monoglyceride is recovered.

According to the present invention, an oil phase is formed of the cosmetic emulsion oil and oxidized petrolatum, with or without additional additive, such as the waxes and co-emulsifiers hereinbefore mentioned, and a separate water phase is prepared containing the neutralizing agent, water and other additives, if desired, such as preservatives, and the like. Both phases are preheated to, say, 55° C.–100° C., stirred and then blended while stirring. Cooling is then effected, with continued stirring, to a temperature between about 25° C.–40° C. A stable W/O emulsion results which is useful as a personal care preparation.

As suggested above, incorporation of conventional minor amounts of other additives is within the purview of the the present invention. For example, up to about 0.3% by weight, based upon the total weight of the emulsion, of a preservative may be present in the claimed compositions without modifying the basic nature of same, Similarly, fragrance and color can be added for aesthetic effects.

EXAMPLES

The following examples are illustrative only and not intended to limit the scope of the invention, except in keeping with the claims hereto appended:

EXAMPLES I, II, & III

Oxidized Petrolatum water-in-oil emulsions

| | I | II | III |
|---|---|---|---|
| Oil Phase | | | |
| Mineral oil | 50.0 | 50.0 | 50.0 |
| Oxidized petrolatum | — | 5.8 | — |
| Microcrystalline wax | 6.7 | 6.7 | — |
| Cetyl palmitate | 4.2 | 4.2 | — |
| Beeswax | — | — | 16.7 |
| Water Phase | | | |
| Sodium borate | 1.1 | 1.1 | 1.1 |
| Deionized water | q.s. | q.s. | q.s. |

Procedure:
heat both water phase and oil phase to 70° C.; add water phase to oil phase with stirring; and cool with stirring to 42° C. and package.

Stability studies:

| 45° C. oven for 30 days | Room temperature for 30 days |
|---|---|
| EX. I Unstable | Unstable |
| EX. II Stable | Stable |
| EX. III Stable | Oil separation |

EXAMPLES IV, V & VI

Oxidized petrolatum water-in-oil emulsions

| | IV | V | VI |
|---|---|---|---|
| Oil Phase | | | |
| Sodium glyceryl oleate phosphate | 3.0 | 3.0 | 3.0 |
| Oxidized petrolatum | 3.0 | 3.0 | 3.0 |
| Stearyl ether of propylene glycol (11) | 3.0 | 3.0 | 3.0 |

-continued

|  | IV | V | VI |
|---|---|---|---|
| Mineral oil | 17.5 | 17.4 | 17.5 |
| Paraffin wax | 3.0 | 3.0 | 3.0 |
| Parabens* | 0.1 | 0.1 | 0.1 |
| Aluminum stearate | — | 1.5 | — |
| Water Phase |  |  |  |
| Calcium oxide | — | — | 0.03 |
| Sucrose | — | — | 0.39 |
| Methyl Parabens | 0.15 | 0.15 | 0.15 |
| Imidazidinyl urea | 0.25 | 0.25 | 0.25 |
| Water | q.s. | q.s. | q.s. |

*Lower alkyl esters of para-hydroxybenzoic acid (Washine Chemical Corporation)

Procedure for Examples IV and V:

heat both phases to 90° C.–95° C.; stir oil phase about 15 minutes while hot; then add the hot water phase and stir 15 minutes at 90° C.–95° C.; and let cool with stirring to about 30° C. and package.

Procedure for Example VI:

add calcium oxide with stirring to the sucrose water solution and heat to 70° C.–75° C.; heat oil phase to 70° C.–75° C.; add water phase to oil phase while hot and stir 15 minutes at 70° C.–75° C.; and cool to about 30° C., while stirring, and package.

Stability studies:

| 45° C. oven for 30 days | Room temperature for 30 days |
|---|---|
| EX. IV Unstable | Separation after 1 week |
| EX. V Slight oil separation | Stable |
| EX. VI Stable | Stable |

EXAMPLE VII

The oxidized petrolatum used in the foregoing examples is from the final stage of a product prepared by blowing air through a feedstock of petrolatum N.F. which is seeded with 2 wt. % of a previously oxidized petrolatum, as follows:

| Oxidation Conditions | Induction Stage | Intermediate Sample | Blowing Stage |
|---|---|---|---|
| Temp. °F. | 235 | 235: 24 hrs. | 210 |
| Time, hrs. | 24 | 210: 121 hrs. | 151 |
| Air Flow, CFM | 2–4.2 | 4.2 | 4.2 |
| Product |  |  |  |
| Lovibond Color, 2" cell | 35y 3r | 40y 5¼r | 40y 5¼r |
| Dissipation Factor at 10° Hz | 0.0034 | 0.0427 | 0.0590 |
| D-974 Acid No., mg/KOH/g | 1.7 | 33.2 | 55.0 |
| D-445 Viscosity, SUS/210° F. | 71 | 105 | 132 |
| D-938 Congealing Pt., °F. | 119 | 117 | 117 |
| D-937 Cone Pen., dmm | 194 | 193 | 190 |
| Odor D-1833 | moderate | slight-moderate | slight-moderate |

Quite surprisingly, oxidized petrolatum can be used under the conditions of the present discovery as a total or partial substitute for conventional W/O emulsifiers, such as beeswax, sorbitan oleate, glycerol oleate, polyglycerol oleate, and the like, which—as is well known—are fraught with drawbacks in the preparation of water-in-oil emulsions which are stable. As is evident from the above examples, oxidized petrolatums of the type herein contemplated form stable emulsions for personal care preparations. What little odor results in the oxidized petrolatum is masked in each of the personal care preparations.

As is also apparent from the above disclosure, oxidized petrolatum can replace beeswax, for instance, in these preparations. In fact, in some cases more stable emulsions result by substitution of the beeswax. The varying and often short supply of beeswax, coupled with its increasing high cost, makes the substitution of beeswax with the readily available and relatively low cost oxidized refined petrolatum of the present invention a commercially very attractive innovation.

Pursuant to statutory requirements, there are described above the invention and what are now considered its best embodiments. It should be understood, however, that the invention can be practiced otherwise than as specifically described above and still be with the scope of the appended claims.

What we claimed is:

1. A stable W/O emulsified cosmetic personal care preparation which comprises about 2.5 to about 75.0 percent by weight cosmetic emulsion oil, about 0.5 to about 7.5 percent by weight oxidized refined petrolatum, said oxidized refined petrolatum being characterized in that it has an Acid No. (ASTM D-974) of 15 to 100, a Saponification No. of 75 to 150, and a Lovibond Color, 2" Cell, of 40y, 5r to 9r, about 0.2 to about 2.0 percent by weight of a polyvalent cationic water-soluble metal salt capable of enhancing the formation of W/O emulsions, and the balance of the preparation is water, the aforesaid concentrations being based upon the total weight, percentagewise, of the preparation.

2. The composition of claim 1 wherein the oxidized refined petrolatum has the following properties:

| Acid No. (ASTM D-974) | 35–75 |
|---|---|
| Saponification No. | 80–125 |
| Lovibond Color, 2" Cell | 40y, 5r–6r |

3. The composition of claim 2 wherein the cosmetic emulsion oil is mineral oil.

4. The preparation of claim 1 in which the cosmetic emulsion oil is present in the concentration of about 3.0 to about 60, the oxidized refined petrolatum in the concentration about 0.7 to about 6.5, and the metal salt in the concentration about 0.4 to about 1.0.

5. The preparation of claim 1 wherein the cosmetic emulsion oil is mineral oil.

6. The preparation of claim 5 wherein the metal salt is sodium borate.

7. The preparation of claim 5 wherein the metal salt is saccharated lime.

* * * * *